United States Patent [19]

O'Lenick, Jr.

[11] Patent Number: 5,049,680

[45] Date of Patent: Sep. 17, 1991

[54] CATIONIC LACTAM POLYMERS AND 1-(3-ALKYL AMINO PROPYL)PYRROLIDONE-2 INTERMEDIATES THEREFOR

[75] Inventor: Anthony J. O'Lenick, Jr., Lilburn, Ga.

[73] Assignee: LCE Partnership, Lake Geneva, Wis.

[21] Appl. No.: 518,491

[22] Filed: May 3, 1990

[51] Int. Cl.$^5$ .................. C07D 207/27; C07D 403/12
[52] U.S. Cl. .................................................. 548/550
[58] Field of Search ............................... 548/543, 550

[56] References Cited

U.S. PATENT DOCUMENTS

| | | | |
|---|---|---|---|
| 3,445,440 | 5/1969 | Susi | 524/156 |
| 3,517,045 | 6/1970 | Susi | 558/27 |
| 4,144,122 | 3/1979 | Emanuelsson | 162/158 |
| 4,215,064 | 7/1980 | Lindemann et al. | 260/403 |
| 4,283,541 | 8/1981 | O'Lenick et al. | 546/336 |

FOREIGN PATENT DOCUMENTS 676116 12/1963 Canada ............................... 548/550

Primary Examiner—David B. Springer

[57] ABSTRACT

The present invention deals with novel quaternary polymeric compounds and their application as softening, anti-tangle, and conditioning agents. The polymers conform to the following structure:

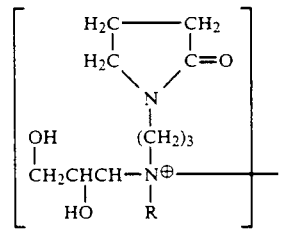

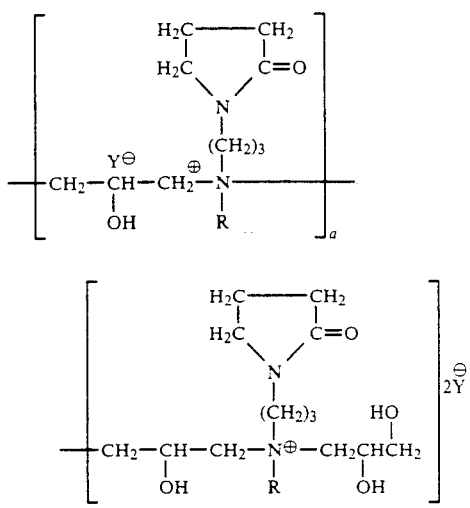

R is selected from $CH_3—(CH_2)_b—$;
$CH_3—(CH_2)_c—(CH=CH)—(CH_2)_d$;
$CH_3—(CH_2)_e—CH(CH_3)—(CH_2)_f—$;
$CH_3—(CH_2)_b—O—R^1—(CH_2)_3—$;
$CH_3—(CH_2)_d—CH(CH_3)—(CH_2)_e—O—R^1—(CH_2)_3—$ and

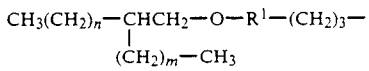

$R^1$ is

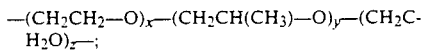

x y and z are independently integers from 0 to 20;
b,c,d,e are independently integers from 5 to 20;
m and n are independently integers from 4 to 20;
a is an integer from 2 to 2,000;
Y is an anionic counter ion needed for charge balance and is selected from chloride, bromide, sulfate, and phosphate.

17 Claims, No Drawings

CATIONIC LACTAM POLYMERS AND 1-(3-ALKYL AMINO PROPYL)PYRROLIDONE-2 INTERMEDIATES THEREFOR

BACKGROUND OF THE INVENTION

1. Field of the Invention

The present invention deals with the composition, and application of novel quaternary polymeric compounds, as softening, anti-tangle, and conditioning agents for use in personal care, textile and related applications. The properties of these novel quaternary polymeric compounds which makes them well suited for these applications is the fact that they are substantive to fibers, hair and skin and also very mild to the skin and eyes. Additionally, unlike many polymers used in the market which are the result of a free radical process, the compounds of this invention are not free radical based, rather are based upon more traditional fatty chemistry, consequently the products are easier to control and give outstanding batch to batch consistency. This consistency is critical to many high performance personal care products.

2. Description of the Art Practices

Standard quaternary compounds are prepared by quaternization of a tertiary amine with such agents as benzyl chloride or di-methyl sulfate or di-ethyl sulfate or methyl chloride. These materials are relatively inexpensive but offer several key disadvantages. These include yellowing of fabrics, a tendency to build-up upon repeated treatment, and variability in hand (i.e. softness and feel). Standard softeners used are selected from the following classes:

Class #1. Alkyl Imidazoline Quaternary Compounds made from the quaternization of an imidazoline made by reacting diethylenetriamine, and a high molecular weight fatty acid such as stearic acid. The standard quaternizing agents are di-ethyl sulfate, or methyl chloride, or di-methyl sulfate, or methyl chloride or benzyl chloride.

Class #2. Alkyl or dialkyl tertiary amines quaternized with benzyl chloride or di-ethyl sulfate or methyl chloride or di-methyl sulfate Class #3. Quaternary compounds of ethoxylated, propoxylated or nonalkoxylated amido amines derived from the reaction of a high molecular weight fatty acid like stearic acid and a polyamine like diethylene triamine. The standard quaternizing agents are di-ethyl sulfate or di-methyl sulfate or methyl chloride or benzyl chloride.

Class #4. Amido amine salts derived from partially acid neutralized amines.

It is known that under certain catalytic conditions, epichlorohydrin reacts with certain alcohols to give an intermediate which can be used to react with tertiary amines to quaternary compounds. U.S. Pat. No. 3,445,440 to Susi (May 1969) and U.S. Pat. No. 3,517,045 to Susi (June 1970) teaches the use of chlorohydroxypropyl ether to alkylate specific tertiary amines which are the reaction product of a primary fatty amine and ethylene or propylene oxide to give compounds conforming to the following structure;

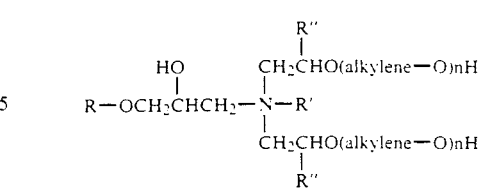

The Susi compounds are used as antistatic agents in polymeric compositions such as polyolefin. The antistatic properties of these compounds are achieved by the minimization of static charges on the polymer surface. These antistatic materials are incorporated into the polymer melt and are effective by virtue of their insolubility in the molten polymer. The quaternary compounds migrate to the polymer surface and are effective antistatic agents.

U.S. Pat. No. 4,144,122 to Emanuelsson issued Mar. 13, 1979 teaches that tallow alcohol and certain other higher molecular weight alcohols and their alkoxylates can be reacted with epichlorohydrin, then subsequently with tertiary amines to give compounds suitable for paper debonding.

U.S. Pat. No. 4,215,064 to Lindemann et al issued July 29, 1980 teaches that phosphobetaines can be prepared by the reaction of a phosphate or phosphite salt with epichlorohydrin under aqueous conditions. U.S. Pat. No. 4,283,541 to O'Lenick, et al. issued Aug. 11, 1981 teaches the process for the preparation of the phosphobetaines described in Lindemann (U.S. Pat. No. 4,215,064). None of these patents teach the compounds of the present invention.

Polyvinylpyrrolidone (pvp), a well known material of commerce, has been prepared by the free radical polymerization of vinyl pyrrolidone using standard free radical initiators. Polyvinylpyrrolidone (pvp) polymers are nonionic in nature, form resinous films and as will become apparent from this disclosure, do not possess the hydrophobic fatty portion of the molecule, which comes from the amino amine raw material.

The reaction of primary amines has been disclosed with butyrolactone in various publications, including U.S. Pat. No. 4,423,040 issued to Rajadhyaksha Dec. 27, 1983, which teaches that 1-substituted azacyclohexan-2-ones can be prepared and used as physiologically active agents. Related patents to Rajadyaksha include U.S. Pat. Nos. 4,525,199; 4,461,638; 4,444,762; 4,562,075; 4,316,893; 4,122,170; 4,405,616; and 4,415,563. None of these referenced patents teach the compounds of the present invention.

OBJECTIVE OF THE INVENTION

It is the object of this invention to produce high molecular weight quaternary polymer compounds that have improved are highly substantive to hair, skin and fibers and are free of the undesirable by-products found in the more irritating standard quaternary compounds. This improved performance relates to the fact that the products of this invention are polymeric and high molecular weight which makes them less likely to cause irritation. The ability to minimize batch to batch variation in the polymeric species produced is another key objective.

It is another objective of this invention to provide a reactive intermediate useful in the preparation of the polymers of this invention. The intermediates are the amino-pyrrolidones which are subsequently reacted with epichlorohydrin to give the compounds of the present invention.

Still another objective of the present invention is to provide polymers based upon ether diamino compounds. These materials are based upon a cyanoethylated alcohol or alcohol alkoxylate and can have varying amounts of alkoxylation present on the hydrophobe. This structural variation offers the possibility of making materials which can be modified to any desired solubility in oil or water.

Still another objective is to provide guerbet alcohol and guerbet alcohol alkoxylate based ether diamine derived pyrrolidones.

THE INVENTION

The monomeric units upon which the present invention is based are novel amino lactams which conform to the following structure:

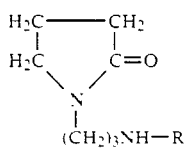

R is selected from $CH_3-(CH_2)_b-$;
$CH_3-(CH_2)_c-(CH=CH)-(CH_2)_d$;
$CH_3-(CH_2)_e-CH(CH_3)-(CH_2)_f-$;
$CH_3-(CH_2)_b-O-R^1-(CH_2)_3-$;
$CH_3-(CH_2)_d-CH(CH_3)(CH_e-O-R^1-(CH_2)_3-$; and

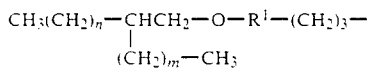

$R^1$ is

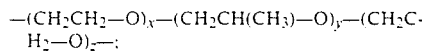

x y and z are independently integers from 0 to 20;
b,c,d,e are each independently integers from 5 to 20;
m and n are each independently integers from 4 to 20.

The reaction of a primary amine or primary amine alkoxylate with acrylonitrile followed by hydrogenation to produce an amino amine or alkoxyaminoamine is well known to those skilled in the art and are commercially practiced by Tomah Products, Milton Wi. The overall reaction is shown below;

Fatty Amines

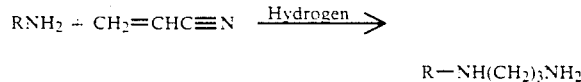

Fatty ether amines

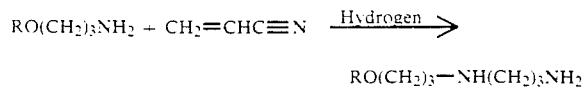

One novel aspect of this invention is the reaction of these diamines with butyrolactone to produce the following intermediate;

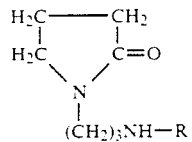

R is selected from $CH_3-(CH_2)_b-$;
$CH3-(CH2)_c-(CH=CH)-(CH_2)_d$;
$CH_3-(CH_2)_e-CH(CH_3)-(CH_2)_f-$;
$CH_3-(CH_2)_b-O-R^1-(CH_2)_3-$;
$CH_3-(CH_2)_d-CH(CH_3)-(CH_2)_e-O-R^1-(CH_2)_3-$ and

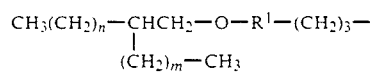

$R_1$ is

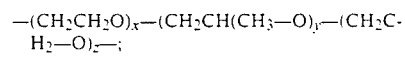

x y and z are independently integers from 0 to 20;
b,c,d,e are independently integers from 5 to 20;
m and n are independently integers from 4 to 20;

Subsequently, these heterocyclic products are polymerized by reaction with epichlorohydrin to give a hydroxypropyl linkage, and the desired high molecular weight quaternary polymeric compounds of this invention.

In a preferred compound R is derived from an alkoxylated ether diamine. Ether diamino compounds of this type are commercially available from Tomah Products Milton Wisconsin. Ether amines used as raw materials in this invention are commercially available and are made by a process which is the reaction of an alcohol or alkoxylate with acrylonitrile in the presence of an alkaline catalyst, e.g., benzyltrimethylammonium hydroxide, potassium hydroxide, sodium methoxide, or sodium hydroxide, to form B-alkoxypropionitrile. The alcohol or alkoxylate and two moles of acrylonitrile may be reacted at temperatures between about 25 C., and about 80 C., in the presence of about 0.1 percent potassium hydroxide for a period of about five to about six hours. The reaction is generally exothermic and external cooling may be required to prevent polymerization of the acrylonitrile. The nitrile is then reduced to the amine and a subsequent mole of acrylonitrile is then reacted.

In still another preferred species Guerbet Alcohols, are used as the raw material to prepare the ether diamine. Guerbet alcohols are highly regiospecifically beta branched alcohols, that have been known since the 1890's when Marcel Guerbet first synthesized them. (M. Guerbet, C.R. Acad. Sci. Paris, 128, 511; 1002 (1899)). These materials are high in molecular weight and are liquid to very low temperatures. Unlike the oxo process and most other processes which result in low molecular weight (e.g. methyl and ethyl groups) random branches on the reactant alcohol, the guerbet reaction gives very specific branching in the alcohol at very high yields. The reaction sequence is the reason for this and is shown as follows;

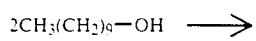

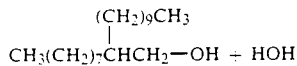

As can be seen by the above reaction the molecules have substitution on the second carbon from the hydroxyl group. This branching has been found to be critical to the preparation of a product having the desired properties. If the branching were on the same carbon as the hydroxyl group, the hydroxyl group would be a secondary one and would be very hindered and have low reactivity. As one moves the branch position away from the beta carbon, the liquidity, and substantivity to hair and fiber decreases.

We have tried to make guerbet based amines using standard chemistry known to those in the art for several years. We were unable to get the desired product in acceptable yield using the technologies currently available, presumably because of the beta branching in the guerbet. This structural feature which is important to our product's performance is a major reason why simple guerbet amines sometimes refereed to as "gurbamines", have been so elusive. The use of the ether amine chemistry not only allowed us to prepare an amine with a high amount of regiospecific beta branching, it also offered a pathway whereby alkoxylation could be introduced into the molecule.

The use of guerbet derived ether amines to prepare compounds of this invention results in substantive liquid products. The high molecular weight of the hydrophobe allows for better oil solubility using these surfactants over conventional nonionic surfactants.

Guerbet alcohols, produced by Exxon Chemicals conform to the following structure;

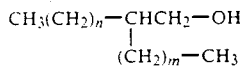

Guerbet alcohol based ether diamines, produced by Tomah Products Division of Exxon, conform to the following structure;

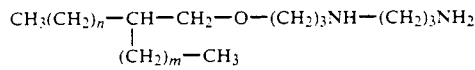

The polymeric quaternary compounds of the invention are the reaction product of the monomeric diamino lactams and epichlorohydrin and conform to the following generic formula;

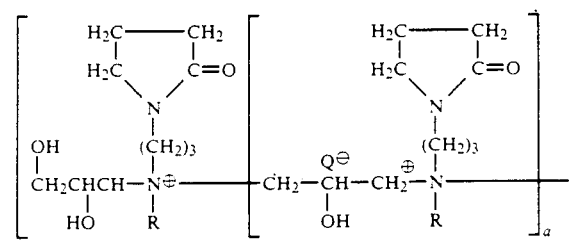

R is selected from $CH_3-(CH_2)_b-$;
$CH_3-(CH_2)_c-(CH=CH)-(CH_2)_d$;
$CH_3-(CH_2)_e-CH(CH_3)-(CH_2)_f-$;
$CH_3-(CH_2)_b-O-R^1-(CH_2)_3-$;
$CH_3-(CH_2)_d-CH(CH_3)-(CH_2)_e-O-R^1-(CH_2)_3-$; and

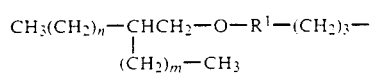

$R^1$ is

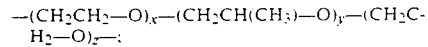

x, y and z are independently integers from 0 to 20;
b, c, d, e are independently integers from 5 to 20;
m and n are independently integers from 4 to 20;
a is an integer from 2 to 2,000;
Q is an anionic counter ion needed for charge balance and is selected from chlorine, bromine, sulfate, and phosphate.

A key feature of the invention is the fact that the molecular weight of the polymeric compounds, and consequently performance of the compounds is controlled by process parameters including the pH at which the polymerization is run, the exact mole ratios of reactants used and the amount and type of solvent used. Of these the most important is pH. The pH of the aqueous solution in which polymerization is conducted has a profound on the molecular weight. At both low and high pH values, the epichlorohydrin will hydrolyze to varying extents, giving a vicinal dihydroxy compound. To the extent the epichlorohydrin hydrolyses it fails to crosslink thereby minimizing the molecular weight achieved by the polymerization.

| pH | Molecular Weight | Example |
| --- | --- | --- |
| 9-10 | 3,500 | 10 |
| 7-8 | 50,000 | 18 |
| 5-6 | 5,000 | 26 |

This ability to vary molecular weight allows a variety of products which can be custom tailored for specific applications, including thickening and lubrication.

EXAMPLES

PREPARATION OF AMINO PYRROLIDONE

The compounds which are useful as intermediates examples 1-9 all conform to the following structure;

$$\begin{array}{c} H_2C\text{------}CH_2 \\ | \quad\quad | \\ H_2C \quad\quad C=O \\ \diagdown N \diagup \\ | \\ (CH_2)_3NH\text{---}R \end{array}$$

EXAMPLE #1

Into a stainless autoclave was introduced 214.0 grams of lauraminopropylamine $CH_3(CH_2)_{11}\text{-}NH(CH_2)_3NH_2$ and 95.0 grams of butyrolactone. The autoclave was sealed and 100 psig nitrogen was applied. The contents were heated to 275 C. and held for eight hours, during which time the pressure rose to about 480 psig. The reaction mass was distilled to give the desired product.

R is $CH_3(CH_2)_{11}$—

EXAMPLE #2

Into a stainless autoclave was introduced 186.0 grams of decylaminopropylamine $CH_3(CH_2)_9NH(CH_2)_3NH_2$ and 95.0 grams of butyrolactone. The autoclave was sealed and 100 psig nitrogen was applied. The contents were heated to 275 C. and held for eight hours, during which time the pressure rose to about 480 psig. The reaction mas was distilled to give the desired product.

R is $CH_3(CH_2)_9$—

EXAMPLE #3

Into a stainless autoclave was introduced 158.0 grams of 2-ethylhexylaminopropylamine and 95.0 grams of butyrolactone. The autoclave was sealed and 100 psig nitrogen was applied. The contents were heated to 275 C. and held for eight hours, during which time the pressure rose to about 480 psig. The reaction mas was distilled to give the desired product.

R is $CH_3(CH_2)_4\underset{\underset{(CH_3CH_2)}{|}}{CH}\text{---}CH_2$—

EXAMPLE #4

Into a stainless autoclave was introduced 157.0 grams of octylaminopropylamine and 95.0 grams of butyrolactone. The autoclave was sealed and 100 psig nitrogen was applied. The contents were heated to 275 C. and held for eight hours, during which time the pressure rose to about 480 psig. The reaction mas was distilled to give the desired product.

R is $CH_3(CH_2)_7$— hours, during which time the pressure rose to about 480 psig. The reaction mas was distilled to give the desired product.

R is $CH_3(CH_2)_9$—.

EXAMPLE #3

Into a stainless autoclave was introduced 158.0 grams of 2-ethylhexylaminopropylamine and 95.0 grams of butyrolactone. The autoclave was sealed and 100 psig nitrogen was applied. The contents were heated to 275 C. and held for eight hours, during which time the pressure rose to about 480 psig. The reaction mas was distilled to give the desired product.

R is $CH_3(CH_2)_4\underset{\underset{(CH_3CH_2)}{|}}{CH}\text{---}CH_2$—

EXAMPLE #4

Into a stainless autoclave was introduced 157.0 grams of octylaminopropylamine and 95.0 grams of butyrolactone. The autoclave was sealed and 100 psig nitrogen was applied. The contents were heated to 275 C. and held for eight hours, during which time the pressure rose to about 480 psig. The reaction mas was distilled to give the desired product.

R is $CH_3(CH_2)_7$—

EXAMPLE #7

Into a stainless autoclave was introduced 298.0 grams of stearylaminopropylamine $CH_3(CH_2)_{17}NH(CH_2)_3NH_2$ and 95.0 grams of butyrolactone. The autoclave was sealed and 100 psig nitrogen was applied. The contents were heated to 275 C. and held for eight hours, during which time the pressure rose to about 480 psig. The reaction product was distilled to give the desired product.

$R = CH_3(CH_2)_{17}$—

EXAMPLE #8

Into a stainless autoclave was introduced 3225.0 grams of a compound, available from Tomah Products, Milton Wi., which conforms to the following structure;

$R\text{---}O\text{---}R^1(CH_2)_3\text{---}NH\text{---}(CH_2)_3NH_2$ $R^1$ is

—$(CH_2CH_2\text{---}O)_{20}$—$(CH_2CH(CH_3)O)_{20}$—$(CH_2CH_2\text{---}O)_{20}$—

$R\text{---}O\text{---}(CH2)3\text{---}NH\text{---}(CH2)3\text{---}NH2$

R is $CH_3(CH_2)_6\underset{\underset{(CH_2)_2CH_3}{|}}{CH}CH_2$— and 95.0 grams of butyrolactone. The autoclave was sealed and 100 psig nitrogen was applied. The contents were heated to 275 C. and held for eight hours, during which time the pressure rose to about 480 psig. The reaction product was distilled to give the desired product.

EXAMPLE #9

Into a stainless autoclave was introduced 495.0 grams of the following compound which is commercially available from Tomah Products Milton Wi;

$R\text{---}O\text{---}(CH_2)_3\text{---}NH\text{---}(CH_2)_3NH_2$

R is

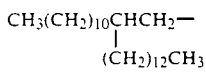

and 95.0 grams of butyrolactone. The autoclave was sealed and 100 psig nitrogen was applied. The contents were heated to 275 C. and held for eight hours, during which time the pressure rose to about 480 psig. The reaction mas was distilled to give the desired product.

EXAMPLE #10

In a suitable reactor equipped with a stirrer, nitrogen sparge and pH probe is added 291.0 grams of the distilled heterocyclic intermediate (Example #1) and 815.0 grams of water. Slowly add 116.5 grams of epichlorohydrin. The degree of polymerization and consequently molecular weight is controlled by the pH of the reaction. During the addition of epichlorohydrin 25% NaOH is added dropwise to keep the pH between 7 and 8. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #11

In a suitable reactor equipped with a stirrer, nitrogen sparge and pH probe is added 263.0 grams of the distilled heterocyclic intermediate (Example #2) and 760.0 grams of water. Slowly, add 116.5 grams of epichlorohydrin. The degree of polymerization and consequently molecular weight is controlled by the pH of the reaction. During the addition of epichlorohydrin 25% NaOH is added dropwise to keep the pH between 7 and 8. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #12

In a suitable reactor equipped with a stirrer, nitrogen sparge and pH probe is added 235.0 grams of the distilled heterocyclic intermediate (Example #3) and 703.0 grams of water. Slowly add 116.5 grams of epichlorohydrin. The degree of polymerization and consequently molecular weight is controlled by the pH of the reaction. During the addition of epichlorohydrin 25% NaOH is added dropwise to keep the pH between 7 and 8. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #13

In a suitable reactor equipped with a stirrer, nitrogen sparge and pH probe is added 234.0 grams of the distilled heterocyclic intermediate (Example #4) and 701.0 grams of water. Slowly add 116.5 grams of epichlorohydrin. The degree of polymerization and consequently molecular weight is controlled by the pH of the reaction. During the addition of epichlorohydrin 25% NaOH is added dropwise to keep the pH between 7 and 8. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #14

In a suitable reactor equipped with a stirrer, nitrogen sparge and pH probe is added 894.0 grams of the distilled heterocyclic intermediate (Example #5) and 2021.0 grams of water. Slowly add 116.5 grams of epichlorohydrin. The degree of polymerization and consequently molecular weight is controlled by the pH of the reaction. During the addition of epichlorohydrin 25% NaOH is added dropwise to keep the pH between 7 and 8. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #15

In a suitable reactor equipped with a stirrer, nitrogen sparge and pH probe is added 405.0 grams of the distilled heterocyclic intermediate (Example #6) and 1043.0 grams of water. Slowly add 116.5 grams of epichlorohydrin. The degree of polymerization and consequently molecular weight is controlled by the pH of the reaction. During the addition of epichlorohydrin 25% NaOH is added dropwise to keep the pH between 7 and 8. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #16

In a suitable reactor equipped with a stirrer, nitrogen sparge and pH probe is added 375.0 grams of the distilled heterocyclic intermediate (Example #7) and 983.0 grams of water. Slowly add 116.5 grams of epichlorohydrin. The degree of polymerization and consequently molecular weight is controlled by the pH of the reaction. During the addition of epichlorohydrin 25% NaOH is added dropwise to keep the pH between 7 and 8. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #17

In a suitable reactor equipped with a stirrer, nitrogen sparge and pH probe is added 3302.0 grams of the distilled heterocyclic intermediate (Example #8) and 6,837.0 grams of water. Slowly add 116.5 grams of epichlorohydrin. The degree of polymerization and consequently molecular weight is controlled by the pH of the reaction. During the addition of epichlorohydrin 25% NaOH is added dropwise to keep the pH between 7 and 8. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #18

In a suitable reactor equipped with a stirrer, nitrogen sparge and pH probe is added 291.0 grams of the distilled heterocyclic intermediate (Example #1) and 815.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 9 to 10. After the addition of epichlorohydrin is complete, the temperature is held between 85–95 degrees C. for two to six hours, pH adjustments are continued as needed. Reaction progress is monitored by percent epoxide analysis and after stripping is very small.

EXAMPLE #19

In a suitable reactor equipped with a stirrer, nitrogen sparge and pH probe is added 263.0 grams of the distilled heterocyclic intermediate (Example #2) and 760.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 9 to 10. After the addition of epichlorohydrin is complete, the temperature is held between 85–95 degrees C. for two to six hours, pH adjustments are continued as needed. Reaction progress is monitored by percent epoxide analysis and after stripping is very small.

EXAMPLE #20

In a suitable reactor equipped with a stirrer, nitrogen sparge and pH probe is added 235.0 grams of the distilled heterocyclic intermediate (Example #3) and 703.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 9 to 10. After the addition of epichlorohydrin is complete, the temperature is held between 85–95 degrees C. for two to six hours, pH adjustments are continued as needed. Reaction progress is monitored by percent epoxide analysis and after stripping is very small.

EXAMPLE #21

In a suitable reactor equipped with a stirrer, nitrogen sparge and pH probe is added 234.0 grams of the distilled heterocyclic intermediate (Example #4) and 701.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 9 to 10. After the addition of epichlorohydrin is complete, the temperature is held between 85–95 degrees C. for two to six hours, pH adjustments are continued as needed. Reaction progress is monitored by percent epoxide analysis and after stripping is very small.

EXAMPLE #22

In a suitable reactor equipped with a stirrer, nitrogen sparge and pH probe is added 894.0 grams of the distilled heterocyclic intermediate (Example #5) and 2021.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 9 to 10. After the addition of epichlorohydrin is complete, the temperature is held between 85–95 degrees C. for two to six hours, pH adjustments are continued as needed. Reaction progress is monitored by percent epoxide analysis and after stripping is very small.

EXAMPLE #23

In a suitable reactor equipped with a stirrer, nitrogen sparge and pH probe is added 405.0 grams of the distilled heterocyclic intermediate (Example #6) and 1043.0 grams of water. Slowly, add 116.5 grams of epichlorohydin. The degree of polymerization and consequently molecular weight is controlled by the pH of the reaction. During the addition of epichlorohydrin 25% NaOH is added dropwise to keep the pH between 9 to 10. After the addition of epichlorohydrin is complete, the temperature is held between 85–95 degrees C. for two to six hours, pH adjustments are continued as needed. Reaction progress is monitored by percent epoxide analysis and after stripping is very small.

EXAMPLE #24

In a suitable reactor equipped with a stirrer, nitrogen sparge and pH probe is added 375.0 grams of the distilled heterocyclic intermediate (Example #7) and 983.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 9 to 10. After the addition of epichlorohydrin is complete, the temperature is held between 85–95 degrees C. for two to six hours, pH adjustments are continued as needed. Reaction progress is monitored by percent epoxide analysis and after stripping is very small.

EXAMPLE #25

In a suitable reactor equipped with a stirrer, nitrogen sparge and pH probe is added 3302.0 grams of the distilled heterocyclic intermediate (Example #8) and 6837.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 9 to 10. After the addition of epichlorohydrin is complete, the temperature is held between 85–95 degrees C. for two to six hours, pH adjustments are continued as needed. Reaction progress is monitored by percent epoxide analysis and after stripping is very small.

EXAMPLE #26

In a suitable reactor equipped with a stirrer, nitrogen sparge and pH probe is added 291.0 grams of the distilled heterocyclic intermediate (Example #1) and 815.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 5 to 6. After the addition of epichlorohydrin is complete, the temperature is held between 85–95 degrees C. for two to six hours, pH adjustments are continued as needed. Reaction progress is monitored by percent epoxide analysis and after stripping is very small.

EXAMPLE #27

In a suitable reactor equipped with a stirrer, nitrogen sparge and pH probe is added 263.0 grams of the distilled heterocyclic intermediate (Example #2) and 760.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 5 to 6. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #28

In a suitable reactor equipped with a stirrer, nitrogen sparge and pH probe is added 235.0 grams of the distilled heterocyclic intermediate (Example #3) and 703.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 5 to 6. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #29

In a suitable reactor equipped with a stirrer, nitrogen sparge and pH probe is added 234.0 grams of the distilled heterocyclic intermediate (Example #4) and 701.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 5 to 6. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #30

In a suitable reactor equipped with a stirrer, nitrogen sparge and pH probe is added 894.0 grams of the distilled heterocyclic intermediate (Example #5) and 2012.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 5 to 6. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #31

In a suitable reactor equipped with a stirrer, nitrogen sparge and pH probe is added 405.0 grams of the distilled heterocyclic intermediate (Example #6) and 1043.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 5 to 6. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #32

In a suitable reactor equipped with a stirrer, nitrogen sparge and pH probe is added 375.0 grams of the distilled heterocyclic intermediate (Example #7) and 983.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 5 to 6. After the addition of epichlorohydrin is complete, the temperature is held between 85-95 degrees C. for two to six hours, pH adjustments are continued as needed. Reaction progress is monitored by percent epoxide analysis and after stripping is very small.

EXAMPLE #33

In a suitable reactor equipped with a stirrer, nitrogen sparge and pH probe is added 3302.0 grams of the distilled heterocyclic intermediate (Example #8) and 6837.0 grams of water. Slowly add 116.5 grams of epichlorohydin. The degree of polymerization and consequently molecular weight is controlled by the pH of the reaction. During the addition of epichlorohydrin 25% NaOH is added dropwise to keep the pH between 5 to 6. After the addition of epichlorohydrin is complete, the temperature is held between 85-95 degrees C. for two to six hours, pH adjustments are continued as needed. Reaction progress is monitored by percent epoxide analysis and after stripping is very small.

APPLICATION EXAMPLES

The quaternary compounds of this invention can be formulated into softeners that are applied directly in aqueous solution by themselves or formulated with anionic, nonionic or amphoteric surfactants and builders to prepare finished conditioner/detergent systems. The level of the quaternary of the present invention is typically used at a weight ratio to water of about 1:10:000 to 1:20 soften fabric. Conditioners and Shampoos using the quaternary employ it at 2% to 30% by weight. Anionic surfactants include lauryl and stearyl sulfate as well as alkylbenzene sulfonates, preferably the sodium salts. Nonionic surfactants include alkylalkoxylates typically having from 10 to 20 carbon atoms in the alkyl group and from 1 to 10 alkylene oxide units (preferably ethylene). Builders include the phosphates STPP and SPP as well as aluminosilicates.

COLOR FASTNESS APPLICATION DATA

Compounds of this invention were compared to standard compounds commercially available using AATCC Test Method 117—1979. The color fastness heat test uses a 400 F. (205 F. hot iron which is applied for 60 and 180 seconds. The color is rated on a 1-5 basis for yellowness, (5 being the most yellow).

| Compound | CAS Number | Yellowness |
| --- | --- | --- |
| Class #1 Compound | 68122-86-1 | 4 |
| Class #2 Compound | 61789-81-9 | 4 |
| Class #3 Compound | 65098-88-6 | 5 |
| Class #4 Compound | 68308-45-2 | 4 |
| Example #16 | | 3 |
| Example #5 | | 2 |
| Example #15 | | 3 |
| Example #22 | | 3 |

| Compound | CAS Number | Yellowness |
|---|---|---|
| Example #31 | | 3 |
| Example #23 | | 2 |
| Example #18 | | 3 |
| Example #25 | | 3 |

WET COMB OUT TEST

A laboratory test is conducted to screen the wet comb properties of a representative member of the family of novel compounds. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water. The hair is then squeezed out and while still damp dipped into a 200 ml solution of 0.2% active quaternary. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12–14 seconds.

| Rinse Conditioner (Wet Comb Out Test) | |
|---|---|
| Product | Time in Seconds |
| Example #10 | 11 |
| Example #18 | 13 |
| Example #26 | 11 |
| Example #14 | 13 |
| Example #22 | 11 |
| Example #30 | 13 |
| Example #12 | 11 |
| Example #20 | 13 |
| Example #17 | 13 |
| Example #25 | 14 |
| Example #33 | 15 |
| Stearyldimethylbenzyl ammonium chloride | 12 |

As can be seen, the compounds of the invention give significant conditioning properties to hair, and coupled with their mild nature with regard to skin and eyes, makes it a prime candidate for cosmetic applications.

What is claimed is:

1. A polymeric quaternary compound conforming to the following formula;

$$\left[ \begin{array}{c} H_2C\text{---}CH_2 \\ | \quad\quad | \\ H_2C \quad C=O \\ \diagdown N \diagup \\ | \\ OH \quad (CH_2)_3 \\ | \quad\quad | \\ CH_2CHCH\text{---}N^{\oplus}\text{---} \\ | \quad\quad | \\ HO \quad R \end{array} \right] \left[ \begin{array}{c} H_2C\text{---}CH_2 \\ | \quad\quad | \\ H_2C \quad C=O \\ \diagdown N \diagup \\ | \\ (CH_2)_3 \\ Q^{\ominus} \quad | \\ \text{---}CH_2\text{---}CH\text{---}CH_2\text{---}N^{\oplus} \\ | \quad\quad | \\ OH \quad R \end{array} \right]_a$$

$$\left[ \begin{array}{c} H_2C\text{---}CH_2 \\ | \quad\quad | \\ H_2C \quad C=O \\ \diagdown N \diagup \\ | \\ (CH_2)_3 \quad HO \\ | \quad\quad | \\ \text{---}CH_2\text{---}CH\text{---}CH_2\text{---}N^{\oplus}\text{---}CH_2CHCH_2\text{---} \\ | \quad\quad | \quad\quad | \\ OH \quad R \quad OH \end{array} \right] 2Q^{\ominus}$$

R is selected from $CH_3\text{---}(CH_2)_b\text{---}$; $CH_3\text{---}(CH_2)_c\text{---}(CH=CH)\text{---}(CH_2)_d$; $CH_3\text{---}(CH_2)_e\text{---}CH(CH_3)\text{---}(CH_2)_f\text{---}$; $CH_3\text{---}(CH_2)_b\text{---}O\text{---}R^1\text{---}(CH_2)_3\text{---}$; $CH_3\text{---}(CH_2)_d\text{---}CH(CH_3)\text{---}(CH_2)_e\text{---}O\text{---}R^1\text{---}(CH_2)_3\text{---}$ and $$CH_3(CH_2)_n\text{---}CHCH_2\text{---}O\text{---}R^1\text{---}(CH_2)_3\text{---}$$
$$|$$
$$(CH_2)_m\text{---}CH_3$$

$R^1$ is $$\text{---}(CH_2CH_2\text{---}O)_x\text{---}(CH_2CH(CH_3)\text{---}O)_y\text{---}(CH_2CH_2\text{---}O)_z\text{---};$$

x y and z are independently integers from 0 to 20;
b,c,d,e are indenpendently integers from 5 to 20;
m and n are independently integers from 4 to 20; a is an integer from 2 to 125;
Q is an anionic counter ion needed for charge balance and is selected from chloride, bromide, sulfate, and phosphate.

2. A compound of claim 1 wherein R is $CH_3\text{---}(CH_2)_b\text{---}$.

3. A compound of claim 1 wherein R is $CH3\text{---}(CH2)_c\text{---}(CH=CH)\text{---}(CH_2)_d\text{---}$.

4. A compound of claim 1 wherein R is $CH_3\text{---}(CH_2)_e\text{---}CH(CH_3)\text{---}(CH_2)_f\text{---}$.

5. A compound of claim 1 wherein R is $CH_3\text{---}(CH_2)_b\text{---}O\text{---}R\text{---}^1(CH_2)_3\text{---}$.

6. A compound of claim 1 wherein R is $CH_3\text{---}(CH_2)_d\text{---}CH(CH_3)\text{---}(CH_2)_e\text{---}O\text{---}R^1\text{---}(CH_2)_3\text{---}$.

7. A compound of claim 1 wherein R is $$CH_3(CH_2)_n\text{---}CHCH_2\text{---}O\text{---}R'\text{---}(CH_2)_3\text{---}$$
$$|$$
$$(CH_2)_m\text{---}CH_3$$

8. A compound of claim 1 wherein x y and z are each 0.

9. A compound of claim 1 wherein Q is chloride.

10. A substituted lactam intermediate conforming to the following formula;

$$\begin{array}{c} H_2C\text{---}CH_2 \\ | \quad\quad | \\ H_2C \quad C=O \\ \diagdown N \diagup \\ | \\ (CH_2)_3NH\text{---}R \end{array}$$

R is selected from $CH_3\text{---}(CH_2)_b\text{---}$; $CH3\text{---}(CH2)_c\text{---}(CH=CH)\text{---}(CH_2)_d$; $CH_3\text{---}(CH_2)_e\text{---}CH(CH_3)\text{---}(CH_2)_f\text{---}$; $CH_3\text{---}(CH_2)_b\text{---}O\text{---}R^1\text{---}(CH_2)_3\text{---}$;

$CH_3-(CH_2)_d-CH(CH_3)-(CH_2)_e-O-R^1-(CH_2)_3-$ and $CH_3(CH_2)_n-\underset{(CH_2)_m-CH_3}{CHCH_2}-O-R^1-(CH_2)_3-$ $R^1$ is $-(CH_2CH_2-O)_x-(CH_2CH(CH_3)-O)_y-(CH_2CH_2-O)_z-;$ x y and z are independently integers from 0 to 20;
b,c,d,e are independently integers from 5 to 20;
m and n are independently integers from 4 to 20.

11. A compound of claim 10 wherein R is $CH_3-(CH_2)_b-$.

12. A compound of claim 10 wherein R is $CH_3-(CH_2)_c-(CH=CH)-(CH_2)_d-$.

13. A compound of claim 10 wherein R is $CH_3-(CH_2)_e-CH(CH_3)-(CH_2)_f-$.

14. A compound of claim 10 wherein R is $CH_3-(CH_2)_b-O-R^1-(CH_2)_3-$.

15. A compound of claim 10 wherein R is $CH_3-(CH_2)_d-CH(CH_3)-(CH_2)_e-O-R^1-(CH_2)_3-$.

16. A compound of claim 10 wherein R is $CH_3(CH_2)_n-\underset{(CH_2)_m-CH_3}{CHCH_2}-O-R'-(CH_2)_3-$.

17. A compound of claim 10 wherein x y and z are each 0.

* * * * *